United States Patent [19]

Dionne et al.

[11] Patent Number: 5,916,554

[45] Date of Patent: Jun. 29, 1999

[54] USE OF POUCH FOR IMPLANTATION OF LIVING CELLS

[75] Inventors: Keith E. Dionne, Rehoboth, Mass.; David W. Scharp, St. Louis, Mo.

[73] Assignee: Washington University, St. Louis, Mo.

[21] Appl. No.: 08/465,195

[22] Filed: Jun. 5, 1995

Related U.S. Application Data

[63] Continuation of application No. 08/333,928, Nov. 3, 1994, abandoned, which is a continuation of application No. 07/922,111, Jul. 29, 1992, abandoned.

[51] Int. Cl.⁶ .......................... A61K 35/12; A61K 35/39; A61K 48/00
[52] U.S. Cl. .................. 424/93.21; 424/93.1; 424/93.2; 424/422; 424/423; 424/424
[58] Field of Search ............................ 435/240.2, 240.21, 435/423, 424, 425, 426, 325; 604/891.1; 424/93.1, 93.2, 93.21, 422–424

[56] References Cited

U.S. PATENT DOCUMENTS

| | | | |
|---|---|---|---|
| 3,648,693 | 3/1972 | Koremura | 604/410 |
| 4,352,883 | 10/1982 | Lim | 435/178 |
| 4,353,888 | 10/1982 | Sefton | 424/424 |
| 4,868,121 | 9/1989 | Scharp et al. | 435/268 |
| 4,963,623 | 10/1990 | Miller et al. | 525/237 |
| 5,071,760 | 12/1991 | Watanabe et al. | 435/394 |
| 5,158,881 | 10/1992 | Aebischer et al. | 435/182 |
| 5,487,889 | 1/1996 | Eckert et al. | 435/93.1 |
| 5,667,961 | 9/1997 | Bernard et al. | 435/1 |

FOREIGN PATENT DOCUMENTS

WO9110425   7/1991   WIPO .

OTHER PUBLICATIONS

Tzuyao, S. Plastic and Reconstructive Surg 1984, 73 p.p. 403–410.
Chacha, P.B. et al. Journ of Bone and Joint Surg 1981, 63–B, No. 2, pp. 244–253.
Cugnenc et al. Chirurgie, 1990 116(6) Abstract only.
Altman, J.J., Horm. Metab. Res. Suppl. 1990, 25 pp. 136–137.
Altman, J.J., Diabetes, Jun. 1986 35(6) Abstract only.
Thompson, J.A. et al., Proc Natl Acad Sci USA, 1989, 86(20) Abstract only.
Culliton Science, 1989, 246 pp. 747–749.
S. Squires Union News, Mass., Health & Science Section, Sep. 22, 1989.
Thompson et al. 1989. Proc. Natl. Acad Sci, USA 86:7928–7932.

*Primary Examiner*—Brian R. Stanton
*Assistant Examiner*—Scott D. Priebe
*Attorney, Agent, or Firm*—Lyon & Lyon LLP

[57] ABSTRACT

A biocompatable and biostable flexible pouch for use e.g., in implanting cell bodies producing therapeutic agents, featuring, in various aspects, either encapsulated or unencapsulated cell bodies contained within the pouch; and a means for attaching the opening of the pouch to a vascularized tissue pedicle.

30 Claims, 1 Drawing Sheet

USE OF POUCH FOR IMPLANTATION OF LIVING CELLS

This is a continuation of application(s) Ser. No. 08/333,928 filed on Nov. 3, 1994, now abandoned, which is in turn a continuation of application Ser. No. 07/922,111 filed Jul. 29, 1992, now abandoned.

BACKGROUND OF THE INVENTION

Therapeutic agents have been implanted into patients for treatment of chronic conditions, deficiencies and disease. In one form of treatment, microcapsules containing cells (or cell clusters) for producing such therapeutic agents, have been used. Specifically, pancreatic islet cell grafts have been performed by implantation either freely into the peritoneal cavity or into an epiploic flap pedicle. (Cugnenc, P. H., et al., Chirurgie 1990, 116(6) p.268–74, and Altman, J. J., Horm. Metab. Res. Suppl. 1990, 25 p.136–7.) Microcapsules containing other cells have been implanted in various areas of the body. One problem with known techniques is that there is no effective way to retrieve the encapsulated cells. In certain instances, it would be desirable to replace such cell capsules because of (a) possible expiration or failure of the cells, (b) a need to change the therapeutic approach or modify the dosage levels, (c) catastrophic failure, or (d) allergic reaction. When using microcapsules, a large number (e.g. hundreds or thousands) are normally employed for dispersion within the individual thereby effectively preventing retrieval.

Another approach which has been suggested is the loading of tissue fragments of insulinomas in permselective tubular membranes which are implanted. (Altman, J. J., Diabetes June 1986, 35(6) p.625–33.) Altman reports that the insulinoma tissue retrieved after implantation showed functionally active endocrine cells and no evidence of graft rejection. However, this is not the optimum environment for long term grafts because the cells are not in close proximity to well-vascularized tissue. Also, the unencapsulated cells do not have optimal diffusional characteristics.

In view of the foregoing, there is a need for implantation of encapsulated or unencapsulated cells into a patient providing optimum conditions for long term cell viability and which permits the complete retrieval of such cells.

SUMMARY OF THE INVENTION

In accordance with the invention, a device and method of use are provided for improving the long-term treatment of a patient by surgically implanting encapsulated or unencapsulated cells or cell clusters producing a therapeutic agent (collectively "cell bodies") and for retrieving such cell bodies. According to the method, a pouch is placed over a vascularized tissue pedicle in an individual's body so that at least part of the pedicle is encased by projecting into the opening of the pouch. The pouch is attached to the pedicle around the pouch opening.

Generally, the amount of cell bodies considered to produce a therapeutically useful amount of secretogogue will depend on systemic requirements and bioactivity of the substance. For insulin secretion, as many as 400,000 cell bodies may be required. In any event, a number of such cell bodies are dispersed onto spaced-apart locations of the pedicle within the pouch. In one technique, the pouch is placed over the pedicle, and the cells are thereafter dispersed (a) onto the pedicle through a syringe which is moved to a number of positions along the pedicle, (b) into the pedicle tissue by the same method, (c) through a cannulated artery, or some other way. Alternatively, spaced cell bodies are dispersed on and adhered to the inner wall of the pouch prior to placing the pouch over the pedicle. In this instance, the pouch is sufficiently close fitting to the pedicle so as to place the cells closely adjacent to the pedicle.

Another aspect of the invention is the retrieval of the cell bodies in the pouch after conclusion of their useful life. In one retrieval technique, the pedicle is surgically removed from the patient along with the pouch and contained cells. Alternatively, the cell bodies are dislodged from the pedicle, as by washing, and collected in the pouch which is removed.

The invention also includes a biocompatible and biostable flexible pouch. A number of spaced cell bodies producing therapeutic agent are adhered to the inner pouch walls for transfer to the pedicle.

DETAILED DESCRIPTION OF THE PREFERRED EMBODIMENTS

Figure 1:
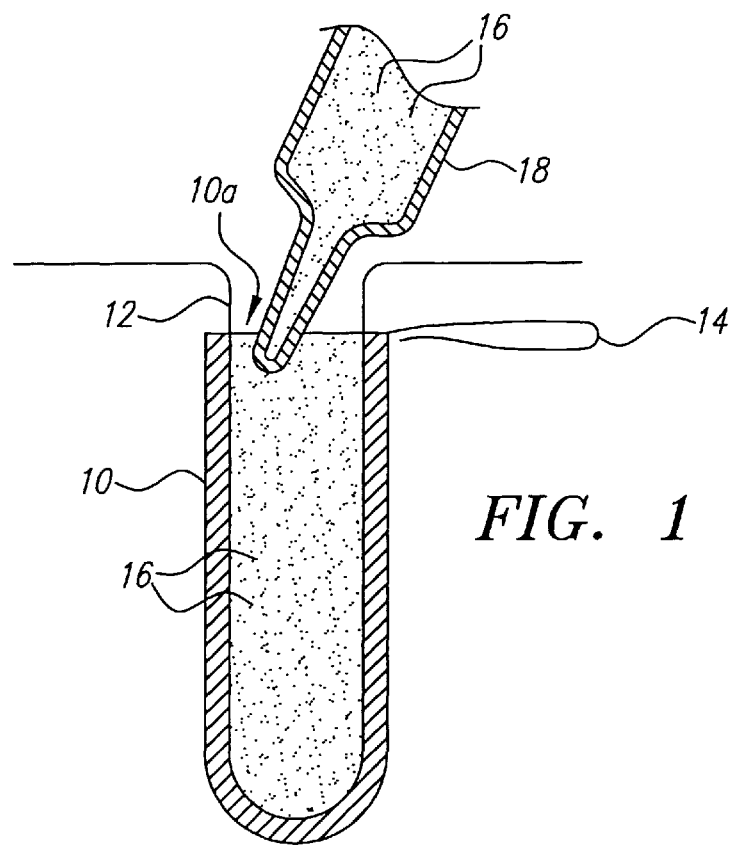
FIG. 1 is a schematic representation of cell bodies being positioned by a syringe into a pouch encasing a pedicle with the pouch in cross-section.

Various aspects of the invention include implanting cell bodies into a tissue pedicle and retrieval of the cell bodies on termination of their useful life or for some other reason. The pouch is surgically attached to a vascularized tissue pedicle in an individual so that at least part of the pedicle is encased by projecting into the opening of the pouch. The cells may be dispersed onto the pedicle surface or into the pedicle itself by a number of techniques described below. At the desired time, the cell bodies are retrieved in the pouch, with or without the tissue pedicle, depending, in part, on the dispersion method chosen.

As used herein, the term "cell bodies" comprise encapsulated or unencapsulated living cells producing a therapeutic agent. The cells may be in any form, including but not limited to cells retained in tissue, cell clusters (e.g. islets), individually isolated cells, and natural and genetically engineered cell lines. Techniques for isolating the cells or tissues which produce therapeutic agents are known to those skilled in the art. For example, islets of Langerhans can be isolated from a large-animal pancreas (e.g. human or porcine) using a combination of mechanical distension and collagenase digestion, as described by Scharp, D. W. et al., (1989) in U.S. Pat. No. 4,868,121.

A large body of literature is available directed to the formation of microcapsules containing living cells. Such microcapsules should be formed of any suitable material which allows passage of the therapeutic agents through pores or voids of a predetermined range of sizes but which protects the cells from potentially harmful large molecules (e.g. antibodies) entering the microcapsules. Suitable microspheres are of a size from about 15 $\mu$m to 600 $\mu$m. They may have a capsule wall formed of alginate-polylysine-alginate configuration (e.g. as disclosed in Lim U.S. Pat. No. 4,352,883) or thermoplastic materials of suitable porosity, (e.g. PAN/PVC as disclosed in Sefton U.S. Pat. No. 4,353,999 or Aebischer et al WO 91/10425). Macrocapsules, (e.g. sizes of about 50–100 $\mu$m diameter and 1 to 30 mm long cylinders) may also be used.

The cell bodies of the present invention can be encapsulated or unencapsulated. However, in view of the mode of delivery of the cell bodies described below, it is preferable to encapsulate if the cell bodies are fragile. Also, encapsulation is useful to avoid immune rejection, particularly if such rejection is not readily avoided in some other way.

The term "pouch" is intended to encompass any structure (preferably flexible) which includes an opening which may be slid over the free distal end of a vascularized tissue pedicle and which is substantially enclosed except for the pouch opening. In this manner, once the pouch is attached at its opening to the pedicle, the cell bodies are retained in a region closely adjacent to the pedicle inside the pouch.

The pouch may have sufficient porosity to permit passage of therapeutic agent produced by the cell bodies into the individual's body cavity surrounding the tissue pedicle.

Alternatively, the pouch may be completely impermeable. Then, the therapeutic agent would be taken up by passing directly into the vasculature of the pedicle.

The pouch is biocompatible and biostable. As used herein, "biocompatible" means that the pouch is formed of a material which does not cause a significant detrimental effect on the transplanted cells or on the patient during a therapeutical useful time, (e.g. a month to a year or more). Moreover, the term means that no specific undesirable cytotoxic or systemic effects are caused by long-term implantation of the pouch. As used herein, the term "biostable" refers to a pouch material which can contain the cell bodies for the total time of implantation.

In a preferred form, the pouch is flexible and closely conforms to the configuration of the pedicle. As used herein, "pedicle" refers to vascularized tissue, in a form capable of being encased by the pouch. The pedicle receives blood supplied by an artery and depends from and projects into a body cavity. If no naturally occurring pedicle projects a sufficient distance for useful encasement, the pedicle may be surgically freed from surrounding tissue. Preferably, the pedicle is not essential to the patient's body functions, thereby permitting its removal during retrieval of the cell bodies. Several known naturally occurring pedicles include fat pads, liver lobes, pancreatic lobes, omental flaps or portions of them.

Appropriate natural vascular pedicles (or their precursors) may be found in the peritoneal cavity. For example, a fat pad fed by a single artery and drained by a single vein may be used. By surgical techniques, such a fat pad pedicle can be isolated away from surrounding tissue so that it hangs free to form a flap of tissue inside the cavity with its own circulation intact.

If no suitable natural pedicle exists, an "artificial pedicle" can be formed by detaching vascularized tissue (e.g. musculofascial tissue) from the individual's body and connecting it to a vascularized source at a selected site on the wall of a cavity (e.g. abdominal cavity) within the same individual to revascularize the tissue.

Another form of artificial pedicle may be formed by transplantation of autologous tissue from one part of the body to another (e.g. musculature vascularized from the leg with blood supply in the middle of the tissue). The cell bodies are placed on the tissue which is folded to wrap around and contain the cell bodies. This is attached to the vasculature within the individuals body cavity (e.g. abdominal cavity) to form the pendant artificial pedicle. Transplanted pedicles in some circumstances may be syngenic or allogeneic. In these instances immunosuppression will generally be required.

The pouch may be formed of a continuous polymeric plastic, such as molded from a flexible sheet and sealed at its edges, or it may be woven from strands in the form of fabrics. Suitable materials of appropriate porosity may be formed from polytetrafluoroethylene (TEFLON) or other plastic materials such as polyolefins (e.g. polyethylene, polypropylene), and polyesters. Silicone rubber may be used as a flexible impermeable pouch material, while a biocompatible material such as titanium may be used as an inflexible, impermeable material.

Also, the pouch may be formed by molding a biocompatible polymer onto the surface of the pedicle and permitting the polymer to set in the form of a continuous pouch conforming to the shape of the enclosed pedicle. This may be accomplished by multiple dipping into a solution of biocompatible polymer (e.g. a cross-linked alginate) to form a pouch which, on setting of the solvent, conforms to the pedicle.

The pouch may also be formed from a biocompatible non-absorbable mesh (e.g. a polyolefin product sold under the trademark MARLEX). Alternatively, it may be formed of a reabsorbable mesh (e.g. such as polydisulfoxane, polyglycolate, or polylactate sold under the trademark VICRYL). In this instance, as the mesh is dissolved, the bag is replaced by a continuous matrix of tissue formed by angiogenesis.

In one advantageous form of the pouch, the cell bodies are contained on the interior wall of the pouch in spaced apart distribution to be uniformly distributed along the vascularized tissue pedicle. These cells can be retained in place by a suitable biocompatible adhesive or glue such as "PRONECTIN" or a viscous hydrogel material such as alginate supplied under the tradename KELTONE HV by Kelco, Inc. For this embodiment, it is preferable to form the pouch of an elastic material, (e.g. silicone rubber) which stretches as the pouch is slid over the pedicle to form a close fit. This is advantageous in that it provides a good distribution of the cells along the pedicle wall.

FIG. 1 illustrates one method for implanting cells in accordance with the invention. Pouch 10 is slid over the vascularized tissue pedicle 12 in a body cavity such as the peritoneal cavity so that at least part of the pedicle is encased by projecting into opening 10a of pouch 10.

Then, the pouch may be attached to the pedicle at opening 10a by a variety of different techniques. In one embodiment, the pouch includes a drawstring 14 which is pulled by the surgeon to tighten the perimeter of the pouch opening around the encased pedicle. In another technique, the pouch is sutured directly to the pedicle. Alternatively, the perimeter of the pouch opening is elastic and attaches by expansion to fit over the pedicle to fit by contraction into a compression fit at the pouch opening. In a further embodiment, an adhesive is applied around the inner periphery of the pouch opening which causes the pouch to adhere to the pedicle. Any of these or other means for attaching the opening of the pouch to a pedicle may be employed so long as such means is capable of long-term retention of the pouch around the pedicle while retaining the cell bodies within the pouch for retrieval.

A number of different techniques may be used to load the capsules onto or into the pedicle. One technique would be to load the cell bodies substantially onto the outer surface of the pedicle as by injection through a tube in spaced apart locations or by adherence from cell bodies layered onto the inner wall of the pouch. In other techniques, the cell bodies are loaded into the interior of the tissue of the pedicle. One technique would be to implant the particles through an artery feeding the pedicle. In another technique, the cell bodies would be loaded through a needle which is inserted into spaced locations throughout the interior of the pedicle. These techniques will be described in more detail hereinafter.

Referring again to FIG. 1, a specific technique is illustrated in which cell bodies 16 are suitably injected through the attached pouch by a tube or syringe 18 which places the cell bodies in spaced apart relationship either deep within the tissue of pedicle 12, on the outer surface of the pedicle, or both. Deep penetration is advantageous because of the proximity to the life sustaining environment provided by the vascular supply carried by the artery to the pedicle.

A suitable syringe technique for loading the cell bodies into the pedicle tissue is as follows. To load the syringe, the cell bodies may be lightly centrifuged and aspirated at a dilution of about 1:20 to 1:50 (e.g. 5 ml of cell bodies in 50 ml media) and deposited through pliable tubing into a 50 ml syringe with an 18 g needle. The needle is then placed at the desired location of the pouch or pedicle (e.g. the distal end of the pedicle). The cell bodies are distributed as by slowly retracting the needle leaving the cell bodies in the needle track. This may be repeated until all cell bodies are injected.

Figure 2:
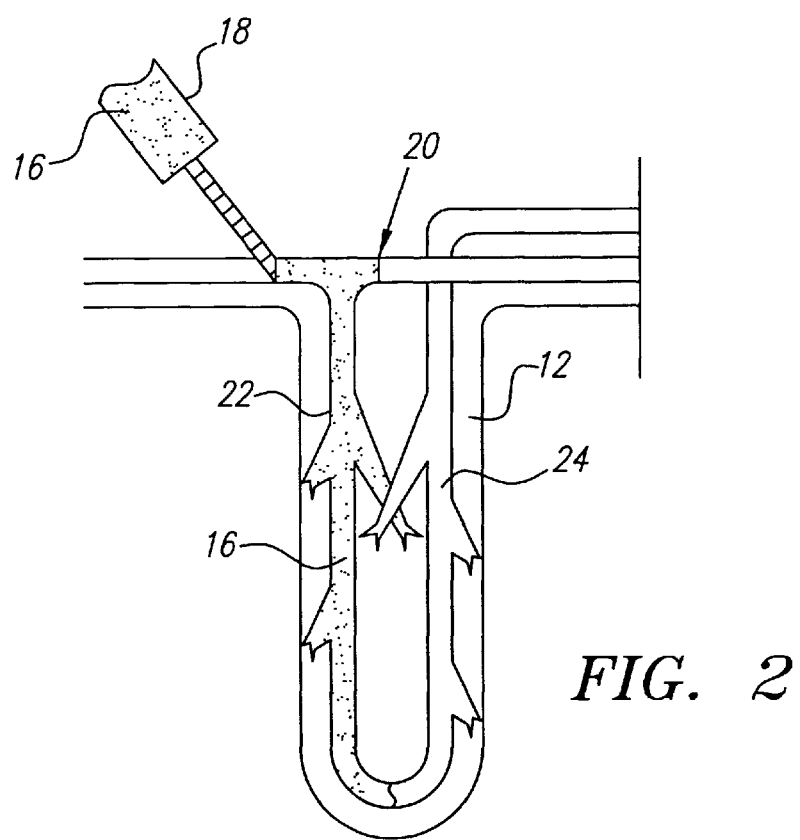
FIG. 2 is a schematic cross-sectional view of a system for positioning cell bodies through a pedicle artery with the pouch removed.

In another embodiment, illustrated in FIG. 2, the cell bodies can be introduced into the pouch by a cannulated artery. That is, the cell bodies may be delivered to various portions of the pedicle through a cannula connected to an artery which feeds the pedicle. This technique may be more difficult to control than injection through the pouch wall. It may be accomplished as follows. The cell bodies are injected from syringe 18 into artery 22 feeding pedicle 12. Conventional directional aids such as fluoroscopy may be used to locate the appropriate artery and direct the cells. If the artery includes a branch downstream from the pedicle, the branch may be temporarily blocked as by clamp 20. At or before the location where the artery narrows to capillary projections, illustrated at the bottom of the artery 22 in FIG. 2 as finger-like projections, the cell body flow terminates because the cell bodies are too large to pass further, as to vein 24. The artery fingers distribute the cell bodies throughout the pedicle.

An advantageous environment for the living cells may be provided by placing a cortex-forming substrate (e.g. a polytetrafluoroethylene fiber such as sold under the trademark GORE-TEX) around the pedicle within the pouch. Angiogenesis may be induced in such substrate by growth factors or the like. The thus-formed substrate serves to provide a scaffolding for the cell bodies.

The cells implanted in accordance with the invention may be retained for long periods of time (e.g. from one month to a year or more).

In another mode of placing the cell bodies, the pouch is preloaded with the cell bodies dispersed on and adhered to the inner wall of the pouch. Spaced cell bodies are attached to the inner pouch wall by a biocompatible adherent substance, such as alginate, coating the pouch wall. Then, the pouch is carefully placed over the pedicle so as to retain the cell bodies in spaced-apart relationship. In this instance, the pouch is preferably form-fitting to the pedicle so that the cell bodies intimately contact the pedicle when the pouch is slid over it. On attaching the pouch to the pedicle, the system is in place for long-term implantation without the necessity of an additional injection step.

One way to conveniently spread the cell bodies along the interior wall of the pouch is to coat flat sheets in a two-dimensional template of the pouch with such adherent substance and to place the cell bodies in spaced apart relationship onto the sheets. Thereafter, the two sheets can be sealed at their periphery as by heat sealing or an adhesive to form a pouch of the desired configuration.

The type of therapy is a major factor in determining the optimum size and porosity characteristics of the pouch as well as the technique for implantation. For example, diabetes therapy uses approximately 35–75 units of insulin per day, requiring about 400,000 islets. Based upon a 150 micron diffusional distance for an interperitoneal implant site, this translates to about 60 square inches of one diffusional surface (i.e. an impermeable pouch) or 30 square inches for two diffusional surfaces (i.e. a permeable pouch). However, a surface area of 60 square inches would require a very large pedicle. Thus, a permeable pouch is preferred for islet implantation.

Moreover, for transplanting a large number of cell bodies, e.g. as is typically required for islets, it is preferred to load deep into the interior of the pedicle tissue (e.g. by arterial or syringe loading). However, where only a smaller number of cells are required for the desired therapeutic dosages, surface loading may be advantageously employed.

Suitable cell bodies are engineered cells which can be used by surface loading and include human growth hormone, erythropoietin, or interleukins.

The pedicle size should be selected to hold the desired number of cells. For example, 400,000 islets occupy a volume of approximately 8 ml. For proper pedicle viability, it is preferred that the pedicle occupy at least about ten times the volume of the cells to be injected. It is most preferred to size the pedicle to be at least 20 times the volume of injected cells. Therefore, a preferred pedicle size for diabetes therapy is on the order of 160 ml or more.

A significant advantage of the invention is the ability to retrieve the cell bodies from the patient after implantation. This permits the flexibility of replacing the cells because of possible expiration or failure of the cells or a need to change the therapeutic approach or modify dosage levels.

A preferred way of retrieving the cell bodies is to surgically remove the pouch, attached pedicle, and cell bodies as a unit from the individual's body. Since the pedicle is preferably selected to be superfluous to the biological function of the individual, the pedicle may be cut in the region of attachment to the pouch to remove it along with the pouch and cell bodies. This may not require a major, open surgical procedure, but can be retrieved by laproscopic procedures currently utilized for such general surgical procedures.

Cell bodies may also be retrieved leaving the pedicle in place. In this instance, the cell bodies are first dislodged from the pedicle and then collected in the pouch. One technique is to wash down the pedicle by a tubing inserted through a surgical incision to cause the cell bodies to flow into the pouch. Thereafter, the pouch and contained dislodged cell bodies are removed from the individual's body leaving the pedicle in place. One problem with this approach is that some of the cell bodies may become lodged in the pedicle and not removed by washing. Thus, this technique is preferably used if retention of some cells would not cause a harmful reaction.

To more clearly illustrate the invention, the following example of its practice is set forth. It is understood that this is not intended to delineate the scope of the claims.

EXAMPLE 1

Pouch Contained Implantation and Retrieval of Microsphere Encapsulate NIT Cells from a Vascular Pedicle The peritoneal cavity of a rat was opened with a midline incision. A fat pad (1 cm×3 cm×0.5 cm~1.5 ml) from the greater mesentery omentum of a Sprague Dawley rat was dissected free from connective tissue and fascia with its circulation remaining intact to that it was in the form of a free floating flap. The flap remained attached to the omentum wall only at the base such that it could be easily removed. The pedicle was then inserted into a loose fitting pouch formed of nylon mesh (sold under the NITEX trademark). The pouch was held in place on the pedicle by means of a suture drawstring (#4 silk) around the pouch opening.

Alginate microcapsules (300–50 $\mu$m diameter) containing NIT cells were prepared by extruding an alginate/cell dispersion ($1 \times 10^6$ NIT cells/ml 1% alginate in 0.9% saline) through a 22 g needle at 0.5 ml/min while flowing air across the needle so as to shear off the dispersion in microdrops which were caught and incubated for six minutes in a bath containing 1% $CaCl_2$ which induced crosslinking. Approximately 200 microcapsules were injected into the pouch through a plastic cannula from a 16 gauge catheter. The abdomen was then closed and the animal returned to its cage. Fourteen days later the abdomen was reopened and the pedicle was severed from the omentum at its base with a scalpel, and removed, with the NITEX pouch intact and all capsules recovered. Encapsulated cells were stained with fluorescein diacetate and propridium iodide to visualize viable cells. A large number of viable cells were found.

What is claimed is:

1. A method for implanting into an individual a plurality of cell bodies secreting an agent, the method comprising the steps of:
   (a) placing or forming a biocompatible and biostable pouch over a vascularized tissue pedicle pendant from and projecting into a cavity of an individual's body so that at least part of the pedicle is encased by the pouch, the part projecting into the opening of the pouch,
   (b) attaching the pouch to the pedicle, and
   (c) dispersing the cell bodies into the pouch or the pedicle.

2. The method of claim 1 in which the cell bodies are contained in microcapsules.

3. The method of claim 1 in which the forming step is performed by molding biocompatible cross-linked alginate onto the surface of the pedicle and permitting the alginate to set in the form of a continuous pouch conforming to the shape of the pedicle.

4. The method of claim 1 in which the attaching step is performed by suturing.

5. The method of claim 1 in which the attaching step is performed by tightening the perimeter of the opening of the pouch around the pedicle.

6. The method of claim 5 which the perimeter of the pouch opening is elastic and attaches by expansion to fit over the pedicle followed by contraction into a compression fit.

7. The method of claim 1 in which the pedicle is naturally occurring.

8. The method of claim 1 in which, prior to step (a), a vascularized tissue mass is detached from the individual's body and connected to a vascular source at a selected site on the wall of the cavity within the individual to revascularize the tissue mass, thereby forming the vascularized tissue pedicle of step (a).

9. The method of claim 1 further comprising:
   (d) surgically removing the pouch, attached pedicle, and contained cell bodies as a unit from the individual's body.

10. The method of claim 1 further comprising:
    (d) dislodging the plurality of cell bodies from the pedicle and collecting them in the pouch, and
    (e) surgically removing the pouch and contained dislodged cell bodies from the individual's body leaving the pedicle in place.

11. The method of claim 1 in which the cell bodies are dispersed by injection from a conduit through the pouch into different sites on the pedicle.

12. The method of claim 1 in which the cell bodies are dispersed into the pedicle through a cannula into an artery feeding the pedicle.

13. The method of claim 1 further comprising placing polytetrafluoroethylene fibers around the pedicle as a substrate for the cell bodies.

14. The method of claim 1 wherein the cell bodies are selected from the group consisting of naturally occurring cells and genetically engineered cells.

15. The method of claim 1 wherein the cell bodies are dispersed into multiple locations of the pouch.

16. The method of claim 1 wherein at least some of the cell bodies are dispersed onto the pedicle.

17. The method of claim 1 wherein at least some of the cell bodies are dispersed into the pedicle.

18. The method of claim 1 in which cell bodies are dispersed on and adhered to the inner wall of the pouch.

19. The method of claim 1 wherein the pouch is flexible.

20. The method of claim 1 wherein the cell bodies are islet cell bodies, the agent is insulin, and a therapeutically effective number of islet cell bodies are dispersed into the pouch.

21. The method of claim 20 wherein the islet cell bodies produce insulin in response to glucose levels.

22. A method for implanting into an individual a plurality of cell bodies producing an agent, the method comprising the steps of:
    (a) placing a biocompatible and biostable pouch over a vascularized tissue pedicle pendant from and projecting into a cavity of an individual's body so that at least part of the pedicle is encased by the pouch, the part projecting into the opening of the pouch, the pouch containing cell bodies dispersed on and adhered to the inner wall of the pouch, and
    (b) attaching the pouch to the pedicle.

23. The method of claim 22 in which the cell bodies are contained in microcapsules.

24. The method of claim 22 wherein the cell bodies are cells present in a tissue.

25. The method of claim 22 wherein the cell bodies are in cell clusters.

26. The method of claim 22 wherein the cell bodies are individually isolated cells.

27. The method of claim 22 further comprising:
    (d) surgically removing the pouch, attached pedicle, and cell bodies as a unit from the individual's body.

28. The method of claim 22 further comprising:
    (d) dislodging most of the cell bodies from the pedicle and collecting them in the pouch, and
    (e) removing the pouch and contained dislodged cell or cell cluster bodies from the individual's body leaving the pedicle in place.

29. The method of claim 22 wherein the cell bodies are islet cell bodies, the agent is insulin, and a therapeutically effective number of islet cell bodies are dispersed on and adhered to the inner wall of the pouch.

30. The method of claim 29 wherein the islet cell bodies produce insulin in response to glucose levels.

* * * * *

UNITED STATES PATENT AND TRADEMARK OFFICE
CERTIFICATE OF CORRECTION

PATENT NO. : 5,916,554
DATED : June 29, 1999
INVENTOR(S) : Dionne, K. et al.

It is certified that error appears in the above-identified patent and that said Letters Patent is hereby corrected as shown below:

Column 1, line 64, change "thereafter", to --therefore--.

Column 4, line 30, change "PRONECTIN " to --PRONECTIN F--.

Signed and Sealed this

Twenty-ninth Day of February, 2000

Attest:

Q. TODD DICKINSON

Attesting Officer

Commissioner of Patents and Trademarks